United States Patent [19]

Spraul et al.

[11] Patent Number: 5,726,570
[45] Date of Patent: Mar. 10, 1998

[54] NMR MEASURING CELL

[75] Inventors: Manfred Spraul, Ettlingen; Martin Hofmann, Rheinstetten; Harald Schwalbe, Steinbach/Taunus, all of Germany

[73] Assignee: Bruker Analytik GmbH, Rheinstetten, Germany

[21] Appl. No.: 758,881

[22] Filed: Dec. 2, 1996

[30] Foreign Application Priority Data

Dec. 28, 1995 [DE] Germany .................. 195 48 977.2

[51] Int. Cl.⁶ .................................................. G01Y 3/00
[52] U.S. Cl. .................................. 324/321; 324/306
[58] Field of Search .............................. 324/321, 318, 324/322, 306, 300, 316

[56] References Cited

U.S. PATENT DOCUMENTS

| | | | |
|---|---|---|---|
| 4,365,199 | 12/1982 | McNair | 324/321 |
| 5,221,903 | 6/1993 | Kasten et al. | 324/318 |
| 5,397,989 | 3/1995 | Spraul et al. | 324/318 |
| 5,545,998 | 8/1996 | Favre et al. | 324/321 |

FOREIGN PATENT DOCUMENTS

| | | | |
|---|---|---|---|
| 109263 | 10/1974 | Germany | G01N 23/24 |
| 4104075 | 3/1992 | Germany | G01N 30/88 |
| 2253904 | 9/1992 | United Kingdom | G01N 30/88 |

OTHER PUBLICATIONS

Rev.Sci. Instrum, vol. 46, No. 9 (Sep. 1975), pp. 1201–1205 Grimalid et al.: "Design of stopped–flow NMR rapid mixing cells".
Journal of Molecular Biology, (1992), vol. 224,No. 3, pp. 837–845.
Nature Structural Biology, vol. 2, No. 10 (1995), p. 865.

*Primary Examiner*—Louis M. Arana
*Attorney, Agent, or Firm*—Paul J. Vincent

[57] ABSTRACT

The invention concerns a NMR measuring cell, in particular one for a flow-through probe head (1) and having at least a first inlet opening (10) to introduce a first injected or pumped reaction liquid into the measuring cell (1) and a second inlet opening (11) for introduction of a second injected or pumped reaction liquid into the measuring cell (1). The measuring cell (1) is subdivided by means of an at least partially movable wall (2) into at least a first chamber (17) which communicates with the first inlet opening and a second Chamber (19) which communicates with the second inlet opening (11). The at least partially movable wall (2) is configured and adapted in such a fashion that directed motion thereof leads to a mixing together of the first reaction liquid separately stored in the first chamber (17) with the second reaction liquid separately stored in the second chamber (19). In accordance with the invention a rapid and homogeneous mixing-together of the two reaction liquids is achieved in milliseconds.

22 Claims, 4 Drawing Sheets

NMR MEASURING CELL

BACKGROUND OF THE INVENTION

The invention concerns a NMR measuring cell, in particular for a flow-through probe head, having a first inlet opening for injecting or pumping a first reaction liquid into the measuring cell and a second inlet opening for pumping or injecting a second reaction liquid into the measuring cell.

This type of NMR measuring cell is known in the art through the publication JOURNAL OF MOLECULAR BIOLOGY, (1992), volume 224, no. 3, pages 733–859.

An ESR measuring cell having the features of the above NMR measuring cell is known in the art through DD 109263. This conventional ESR measuring cell has means for disposing the reaction liquids near the measuring volume. Rotation of a cylindrical mixing chamber block causes introduction of the liquids into a mixing chamber via leads. The mixing chamber is located directly in front of the measuring volume.

NMR flow-through measuring cells are, in particular, utilized in molecular biological proton folding applications. These applications examine, for example, polypeptide chains using NMR spectroscopy. The folding of these chains in combination with ribosomes is an important step for the transfer of genetic information in biological processes. The reaction mechanism and the precise motion dependence of these proteins is in principle up to this point in time, not fully studied and understood. The reaction mechanisms and the shape changes of these types of proteins which are important to biological reactions can be investigated in a time-dependent fashion using nuclear magnetic resonance spectroscopy. The reaction time constants are in the range of milliseconds to seconds. Consequently, it is important to effect the protein reactions being studied as quickly as possible, for example, in the range of milliseconds.

Described in the journal NATURE STRUCTURAL BIOLOGY, volume 2, no. 10 (1995), page 865 is a method in which the α lactobumin (BLA) is investigated in a series of one-dimensional nuclear magnetic resonance experiments. The reaction mechanism is triggered through the mixing of two reaction liquids. One reaction liquid contains the BLA. The BLA folding, which typically occurs with a time constant of 40 ms in the presence of $Ca_{2+}$, is triggered by a rapid introduction of a second reaction liquid into the NMR measuring cell, the two reaction liquids being injected into the measuring cell. It has been experimentally determined that only after a mixing time of approximately 1 second are the two reaction liquids mixed together to an acceptable degree of homogeneity.

The publication JOURNAL OF MOLECULAR BIOLOGY, volume 224, no. 3, page 837–845 describes a similar method for investigation of enzyme folding. In this method the reaction liquids are brought together by means of a so-called Hamilton injector using a conventional T-jet mixer and introduced into a NMR measuring cell. The rapid mixing of the two reaction liquids triggers the reaction and the associated subsequent protein folding is investigated. The apparatus, including injection by means of the so-called Hamilton injectors, is thoroughly described in an article by Fersht, A. R. and Jakes, R. in Biochemistry, 14, (1975), pages 3350 to 3356. The conventional method injects two reaction liquids into a measuring cell to bring the reaction liquids together and to mix them.

The conventional methods have the disadvantage of requiring substantial mixing times before the two reaction liquids are mixed together in a sufficiently homogeneous manner. This can take up to 1 second or longer, wherein the investigation of reaction times for protein folding which lie significantly under one second, i.e. in the millisecond range, would be interesting. The conventional method leads to displacement and inhomgeneous thinning of the injected reaction liquid, particularly with large sample amounts.

It is consequently the purpose of the present invention to present a NMR measuring cell which leads to a reliable rapid and homogeneous mixing of two reaction liquids within milliseconds.

SUMMARY OF THE INVENTION

This purpose is achieved in that the measuring cell is subdivided, by means of an at least partially movable wall, into at least a first chamber communicating with a first inlet opening and a second chamber communicating with a second inlet opening, wherein the at least partially movable wall is arranged and configured in such a fashion that a controlled movement of the at least partially movable wall leads to a mixing together of the first reaction liquid stored in the first chamber and the second reaction liquid stored in the second chamber.

In this manner the purpose of the invention is completely achieved. The separate storage of the two reaction liquids in the measuring cell guarantees that sufficient time is available in order to introduce the two reaction liquids in a homogeneous, careful, and complete manner into the measuring cell. Only after the two reaction liquids have already been introduced into the measuring cell and initially separately stored are they brought into contact with another and thoroughly and quickly mixed together by means of rapid motion of the at least partially movable wall, to facilitate a rapid and homogeneous mixing within milliseconds. In contrast to the conventional method which introduces and mixes the reaction liquids by means of injection, the method in accordance with the invention facilitates measuring procedures which allow for large quantities of reaction liquids to be combined with each other in a rapid fashion.

In an embodiment of the measuring cell in accordance with the invention the first chamber has a first outlet opening and the second chamber has a second outlet opening. This has the advantage that the two chambers can each be filled independently and separately from each other.

It is advantageous when the measuring cell has a cylindrical shape. This has the advantage that the symmetry properties of the conventional NMR probe head configurations can be taken into consideration.

In an embodiment of the measuring cell in accordance with the invention, the at least partially movable wall has mixing means, for example wings or diagonal openings. This has the advantage that the rapid motion of the at least partially movable wall simultaneously leads not only to removal of the separation between the two reaction liquids, but also facilitates their mixing, wherein a rapid homogeneous reaction mixture is established.

It is advantageous when the at least partially movable wall comprises at least two components which are movable relative to each other and which interlockingly engage each other. This has the advantage that the liquids can initially be separately stored in the differing chambers defined by the mutually interlocking portions. The two reaction liquids can first come in contact and react with each other when the two mutually interlocking components are moved relative to each other.

In an improvement in this embodiment the at least partially movable wall has a first component comprising wings and a second component having windows, wherein, in a first separating position of the wall, the wings interlockingly engage into associated windows in such a fashion that the first and second reaction liquids are stored separately and in a second mixing position of the wall, the wings open the windows in such a fashion that a mixing of the first and second reaction liquids takes place. This measure has the advantage that the dove-tailing of the mutually interlocking wings and windows initially facilitates complete and definitive separate storage of the reaction liquids. Subsequent to the time at which the liquids are filled into the appropriate chambers it is possible for a rapid motion of the wing component relative to the window component to not only cause openings between the first and second chambers, but the relative motion between the window and wing components also causes a mixing together of the two mutually reacting liquids.

In an improvement of this embodiment, the two moving components rotate relative to each other. This has the advantage that the rotational motion facilitates a rapid relative motion between the two movable parts and a good mixing together of the two reaction liquids in a mechanically simple manner, wherein a good fitting-together of the two mutually interlocking components is also guaranteed.

In an improvement in this embodiment one part of the at least partially movable wall is stationary within the measuring cell and the second component rotates about an axis disposed vertically in the center of the measuring cell. This measure has the advantage that one part of the measuring cell can be stationary so that only one moving part is necessary. The moving component is, for its part, rotationally borne in the measuring cell and rotates about a vertical axis in the measuring cell. In this manner, an advantageous cylindrical configuration of the measuring cell is given, wherein the rotating component rotates about the central axis of the cylinder-shaped measuring cell. The rotating component maintains its geometrical configuration during rotation relative to the side walls of the measuring cell, while nevertheless moving relative to the stationary installed component of the at least partially movable wall.

It is advantageous when the stationary component has windows and the movable component wings. This has the advantage that wings fashioned on the movable component move in a propeller-like fashion through the reaction liquid by means of the motion of the movable wall relative to the stationary wall and cause an homogeneous and rapid mixture of the two reaction liquids.

In an advantageous embodiment the wall separates four, in general 2n, chambers, wherein n is a whole number and each chamber has an inlet opening. This has, for example when mixing two reaction liquids, the advantage that the two oppositely lying chambers can be filled with the same reaction component and the intervening chambers can be filled with the reaction partner. In this fashion the reaction area which is available to the two reaction liquids is increased which, for its part, leads to a more rapid and homogeneous mixing of the two reaction liquids.

In an advantageous improvement of this embodiment the NMR measuring cell is characterized in that the at least partially movable wall has a cross-shaped cross section.

This has the advantage that the wall can be easily disposed in a cylinder-shaped measuring cell. When, for example, one component of the movable wall rotates relative to the other component this cylindrical symmetry of the measuring cell allows the cross-shaped configuration to guarantee a sealing separation between the reaction liquids before triggering the reaction. However, the e.g. rotational motion of the rotating part does not change the geometrical orientation of the rotating part with respect to the cylindrically shaped measuring cell, wherein the rotational motion facilitates both separation by means of the interlockingly engaging stationary and movable components as well as mixing.

In another embodiment the wall and/or the measuring cell are configured in such a fashion that the wall is at least partially retractable from the measuring cell to facilitate the mixing of two reaction liquids. This measure has the advantage that the two reaction liquids can initially be introduced and separately stored in the measuring cell in a relatively simple manner. The two reaction liquids are then subsequently rapidly brought into mutual reaction when the movable wall is at least partially retracted out of the cell.

In an improvement of this embodiment, a seal is provided for between the wall and measuring cell, to store the first and second reaction liquids in a sealing fashion in the first and second chambers respectively. This has the advantage that the two chambers can initially be sealed-off from each other, wherein the two reaction liquids can be introduced and stored separately in the measuring cell. When preparations for the measurement are sufficiently completed and after the reaction liquids have been brought into the measuring cell, the reaction can be induced through at least partial retraction of the movable wall from the measuring cell.

In an improvement of this embodiment the at least partially movable wall has mixing means, for example, wings or diagonal openings. This measure has the advantage that retraction of the at least partially movable wall simultaneously leads to a mixing of the two reaction liquids, wherein the pulling-out and the motion which is thereby caused simultaneously serves as motional energy for mixing.

It is advantageous when the mixing of the two reaction liquids is caused by a vertical motion of the wall parallel to the longitudinal axis of the measuring cell. This has the advantage that a cylindrical measuring cell can also be easily configured in such a fashion that the two chambers are initially kept separate from each other and are subsequently brought into reaction contact with another.

In an improvement of this embodiment, the wall can be pulled through an upper end of the measuring cell out of the measuring cell. This has the advantage that a relatively compact configuration is guaranteed which is mechanically simple to manufacture.

It is advantageous within the context of this embodiment when the wall includes a pipe-shaped component, wherein the first chamber of the separated measuring cell is located within the pipe-shaped component and the second chamber is formed between the outer wall of the measuring cell and the outer surface of the pipe-shaped component. The high symmetry of this configuration is particularly advantageous for precise NMR measurements. The cylindrical symmetry of the pipe-shaped component additionally facilitates a simple removal of the pipe-shaped component, for example through the upper end of the measuring cell, wherein a compact configuration leading to a rapid and reliable mixing is guaranteed.

In a further improvement of this embodiment the pipe-shaped component is configured as a hollow cylinder and the measuring cell has a ring-shaped gap on its upper end, wherein mixing Of the two reaction liquids is effected by the retraction of the hollow cylinder through the ring-shaped gap. This has the advantage that a cylindrical symmetry can be utilized and a ring-shaped gap can be provided with, for example, an O-ring seal. In this manner the two reaction liquids are initially separately stored in the measuring cell. Following preparation of the reaction liquid and the measurement the cylinder-shaped part of the separation wall is pulled through the ring-shaped gap formed in the upper portion of the measuring cell, wherein the two reaction liquids react with each other in a rapid manner.

It is advantageous when the wall comprises a radially extended base on one end thereof to strengthen mixing of the two reaction liquids. This has the advantage that the retraction of the movable wall simultaneously leads to a good mixing together of the reaction liquids.

In an advantageous improvement of this embodiment, the base has diagonal bores or wings. This has the advantage that additional mixing mechanisms are provided for on the base which lead to a better and more rapid mixing of the two reaction liquids.

In an advantageous method in accordance with the invention for the rapid mixing of at least two reaction liquids in the measuring cell of a NMR spectrometer, an elution corresponding to a chromotography signal peak (LC peak) is separated from a column of a liquid chromotography apparatus (LC column) and introduced on-line as a reaction liquid into a chamber of the measuring cell. This has the advantage that the NMR measuring cell in accordance with the invention is also suitable for coupled LC-NMR measurements. The on-line coupling of LC and NMR is e.g. discussed in DE 41 04 075 C1.

Further advantages of the invention can be derived from the description and the drawing. The above mentioned features and those to be described further below can be utilized in accordance with the invention individually or collectively in arbitrary combination. The embodiments shown and described are not to be considered as exhaustive enumeration rather have exemplary character only for illustration of the invention.

DESCRIPTION OF THE PREFERRED EMBODIMENT

The figures are partially shown in a very schematic fashion in order to emphasize the essential features of the invention. In these representations the dimensions are only exemplary and are not necessarily to be taken to scale.

Figure 1:
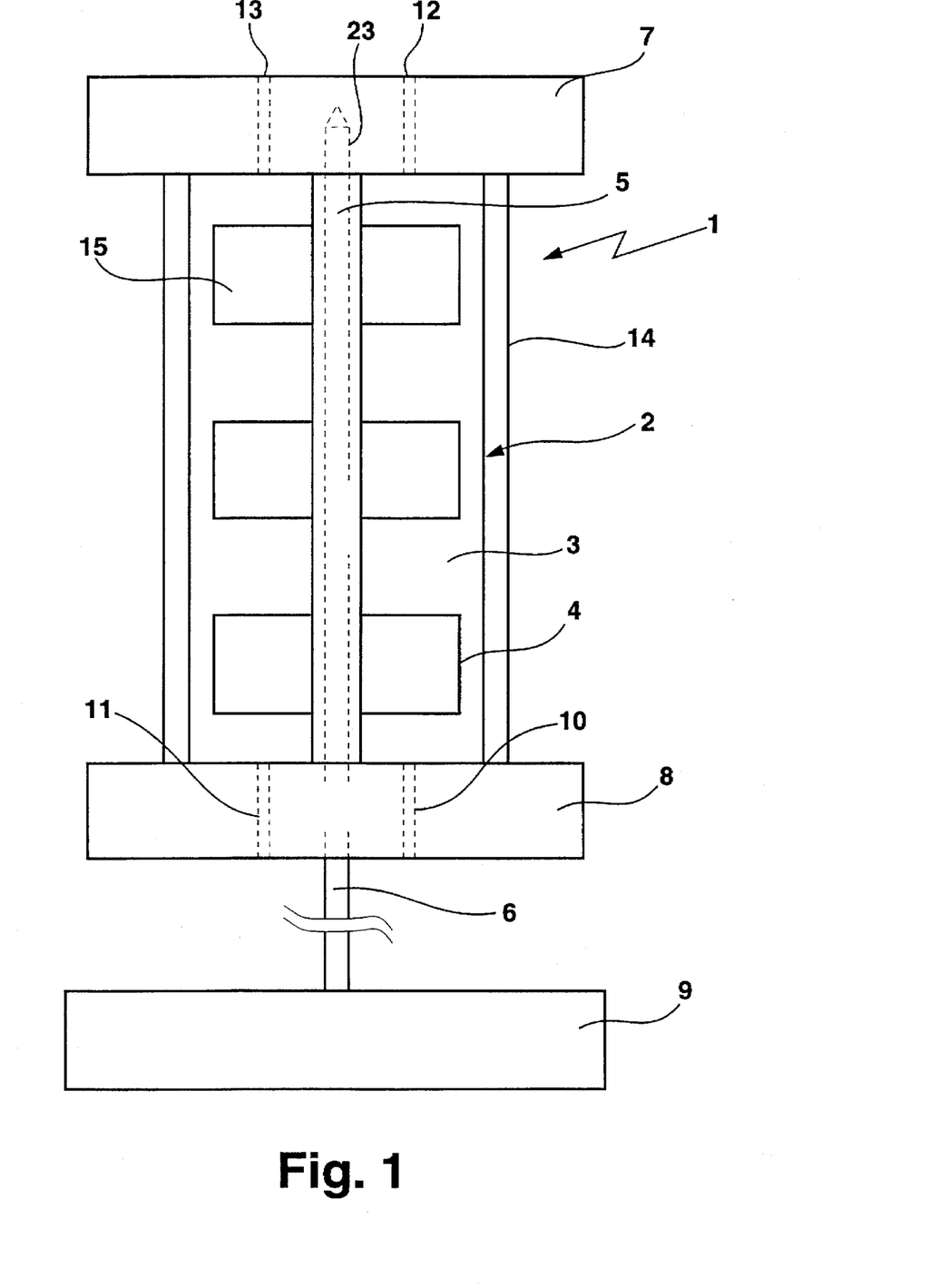
FIG. 1 shows a vertical cut through a measuring cell with a mixing cross configuration for the at least partially movable wall having four mixing chambers.

FIG. 1 shows a measuring cell 1 which, for example, is configured for NMR flow-through measurements, comprising an upper component 7, a lower component 8 as well as a side wall 14 connecting the upper and lower components. A mixing cross configuration 2 is located within the cylindrically shaped measuring cell 1 and is coaxially disposed within the measuring cell 1. This vertical cut through the measuring cell 1 in accordance with FIG. 1 illustrates two components of the mixing cross configuration 2. The first component 3 has window openings which interlockingly engage wings 15 of a wing component 4. In the embodiment in accordance with FIG. 1, the window component 3 is stationary within the measuring cell 1 and the wing component 4 comprises a central axis 6 which is disposed coaxially with respect to the cylindrical side wall 14 of the measuring cell 1. The window component 3 has a central bore 5 through which the axis 6 of the wing component 4 penetrates. The axis 6 is borne in a pivotable fashion in a rotation mounting 9 and is seated in a guide means 23 of the upper component 7.

The lower component 8 of the measuring cell 1 has a plurality of inlet openings, for example, a first inlet opening 10 as well as a third inlet opening 11. A first outlet opening 12 and a third outlet opening 13 are located in the upper component 7 of the measuring cell 1 and are associated with these inlet openings 10, 11 in the lower component 8 of the measuring cell 1. As described further below, the first inlet opening 10 communicates with the first outlet opening 12 and the third inlet opening 10 communicates with the third outlet opening 13 in that state of the movable wall in which the reaction liquids are separated.

Figure 2:
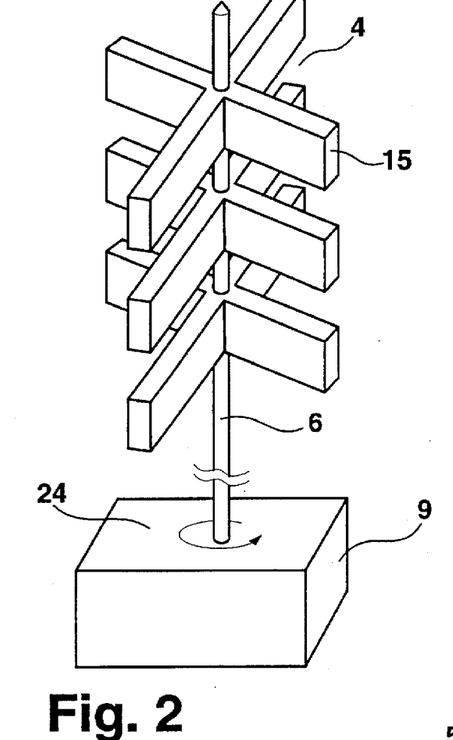
FIG. 2 shows a perspective representation of a mixing component of the mixing cross configuration in accordance with FIG. 1 which is movable and which has wings.

FIG. 2 shows a perspective view of the component 4 of the at least partially movable wall having wings 15 in accordance with the mixing cross configuration 2 of FIG. 1. The wing component 4 has a central axis 6 which is mounted in a rotating fashion on a rotation mounting 9. The wing component 4 has a plurality of cross-shaped wings 15 each of which is securely mounted to the rotational axis 6. The wings 15 are disposed symmetrically about the rotational axis 6 in the embodiment of FIG. 2. Rotation of the rotational axis 6 in the direction of arrow 24 causes the wings 15, which are securely mounted to the rotational axis 6, to likewise be brought into rotational motion.

Figure 3:
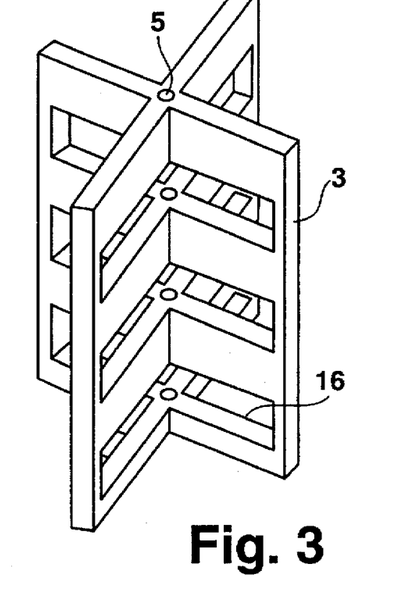
FIG. 3 shows a perspective representation of the other component of the mixing cross in accordance with FIGS. 1 and 2 which can be stationary in the measuring cell and which has windows.

A perspective view of the window component 3 is represented in FIG. 3. The window component 3 has a central bore 5 through which the rotational axis 6 of the wing component 4 penetrates. The windows 16 formed in the window component 3 are dimensioned in such a fashion to guarantee an interlocking engagement between the wings 15 of the wing component 4 into the window 16 of the window component 3. The wing component 4 is movable and the window component 3 is stationary in the measuring cell 1 in the embodiment in accordance with FIGS. 1 through 3. Other embodiments are possible with which the wing component 4 is stationary and the window component 3 is movable or in which a relative motion between the window component 3 and the wing component 5 is effected.

Figure 4:
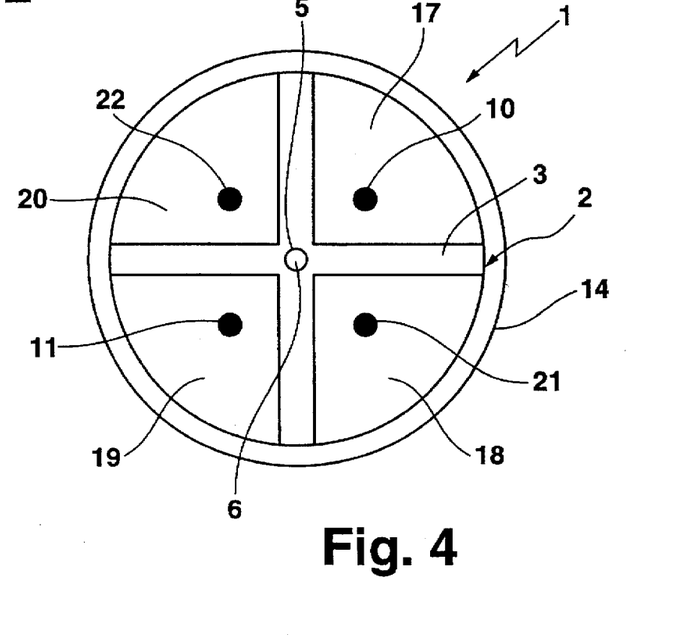
FIG. 4 is a plan view of the cross configuration in accordance with FIGS. 1, 2 and 3.

FIG. 4 shows a schematic plan view, from below, of the measuring cell 1 in accordance with the invention having a mixing cross configuration 2 in accordance with FIGS. 1 through 3. The measuring cell 1 has a cylindrical side wall 14. The mixing cross configuration 2 is disposed in the cylindrical measuring cell 1 in such a fashion that a interlocking fitting of the mixing cross 2 within the inner surface of the side wall 14 of the measuring cell 1 is effected. The central bore 5 of the mixing cross configuration 2 and the central axis 6 are disposed coaxially in the measuring cell 1. The symmetric cross-shaped configuration allows for a division of the measuring cell 1 into four separate chambers 17, 18, 19 and 20, wherein each chamber has an associated inlet opening 10, 21, 11, 22.

In the embodiment in accordance with FIGS. 1 through 4, the inlet openings 10, 21, 11, 22 are located in the lower component 8 and the outlet openings 12, 13 in the upper component 7 of the measuring cell 1. In other embodiments, one or a plurality of inlet openings can be formed in the upper component of the measuring cell as well as one or a plurality of corresponding outlet openings in the lower component of the measuring cell.

In order to operate the measuring cell 1 in accordance with FIGS. 1 through 4, the movable wing component 4 is rotated about its rotation mounting 9, for example in the rotation direction of the arrow 24, up to establishment of interlocking engagement of the wings 15 of the wing component 4 in the corresponding apertures 16 of the window component 3. In this fashion the window openings 16 of the window component 3 are sealed by the wings 15 of the wing component 4 to subdivide the measuring cell 1 into four separate chambers 17, 18, 19, 20. In this position the reaction liquids are introduced into the measuring cell 1 through the inlet openings 10, 21, 11, 22. For example, when two reaction liquids are to be mixed with each other the first reaction liquid is filled into the chambers 18 and 20 using inlet openings 21 and 22 and the second reaction liquid is introduced into chambers 17 and 19 using inlet openings 10 and 11. When the measuring cell is prepared in this state and filled up with the appropriate reaction liquids and when all electronic, computer, or other preparations necessary for carrying out the desired NMR measurement have been completed, the two reaction liquids are mixed by rotating the wing component 4 about its rotational axis 6. The rotational motion causes the wing component 4 to open the windows 16 as a result of which a connection is established between the reaction chambers 17, 18, 19 and 20. The rotational motion of the wing component 4 simultaneously leads to a rapid and homogeneous mixing of the two reaction liquids along the entire vertical height of the measuring cell 1.

With the embodiment in accordance with FIG. 4 it is, for example, possible to carry out NMR measurements with at least two components within milliseconds. The measurements can also be cyclically repeated. In the embodiment according to FIGS. 1 to 4, four mixing chambers are provided for, but other embodiments having two mixing chambers or an arbitrary other number of mixing chambers are also possible. The mixing cross configuration 2 in accordance with figures 1 through 4 is particularly well suited for use with a flow-through probe head of a NMR measuring cell 1. The base plate 8 having inlet bores 10, 11, 21 and 22 has a sealed central bore for the acceptance of the rotational axis 6 of the wing component 4. In accordance with the embodiments according to FIGS. 1 through 4, the lid plate 7 has drain bores 12, 13. The number of inlet bores 11, 21, 33 and drain bores 12, 13 correspond to the number of chambers 17, 18, 19, 20 of the mixing cross 2, wherein the embodiment of FIG. 4 has four inlet 10, 21, 11, 22, four outlet openings and four chambers 17, 18, 19, 20.

The measuring cell can be manufactured from a glass tube and have a height of 30 mm and a diameter of 8 mm. The mixing cross 2 can have two, three or more windows 15 and wings 16 and is ideally manufactured from susceptibility-compensated glass or from material having low proton content. The number of wings 15 of the wing component 4 corresponds to the number of windows 16 of the window components 3 and the central part of each wing 15 has a bore for acceptance of the rotation axis 6. It is advantageous when the wings 15 are cut out of the windows 16 of the mixing cross configuration 2 in order to guarantee optimal sealing. The mixing wings 15 are also preferentially manufactured from a susceptibility-compensated glass or from material with low proton content. The axis 6 serves for attachment of the mixing wings 15 and is rotated by controlled rotation of the wings 15 using a drive mechanism (not shown), wherein the rotation axis 6 is also preferentially manufactured from material of low proton content or from compensated glass. The mixing cross mechanism 2 drive is preferentially disposed outside of the measuring region.

The shape of the mixing cross 4 having, for example, two, three, four or more chambers 17, 18, 19, 20 allows for variation of the number and fractioning of the starting elements. The chambers 17, 18, 19, 20 are initially separated from each other and closed by the mixing wings 15. The inlets 10, 11, 21, 22 and outputs 12,13 of the chambers 17, 18, 19, 20 are connected to the base of the probe head by means of capillaries. The chambers 17, 18, 19, 20 can be filled by injection or, preferentially, by pumping. Following the technical preparations of the starting elements as well as the reagent, mixing is effected through a single rapid rotation of the mixing wings through, for example, 90°, 180°, 270° or 360°. The measurement can start directly following rotation. This procedure is effected in such a fashion that it can run completely automatically and be repeated as often as desired.

Figure 5:
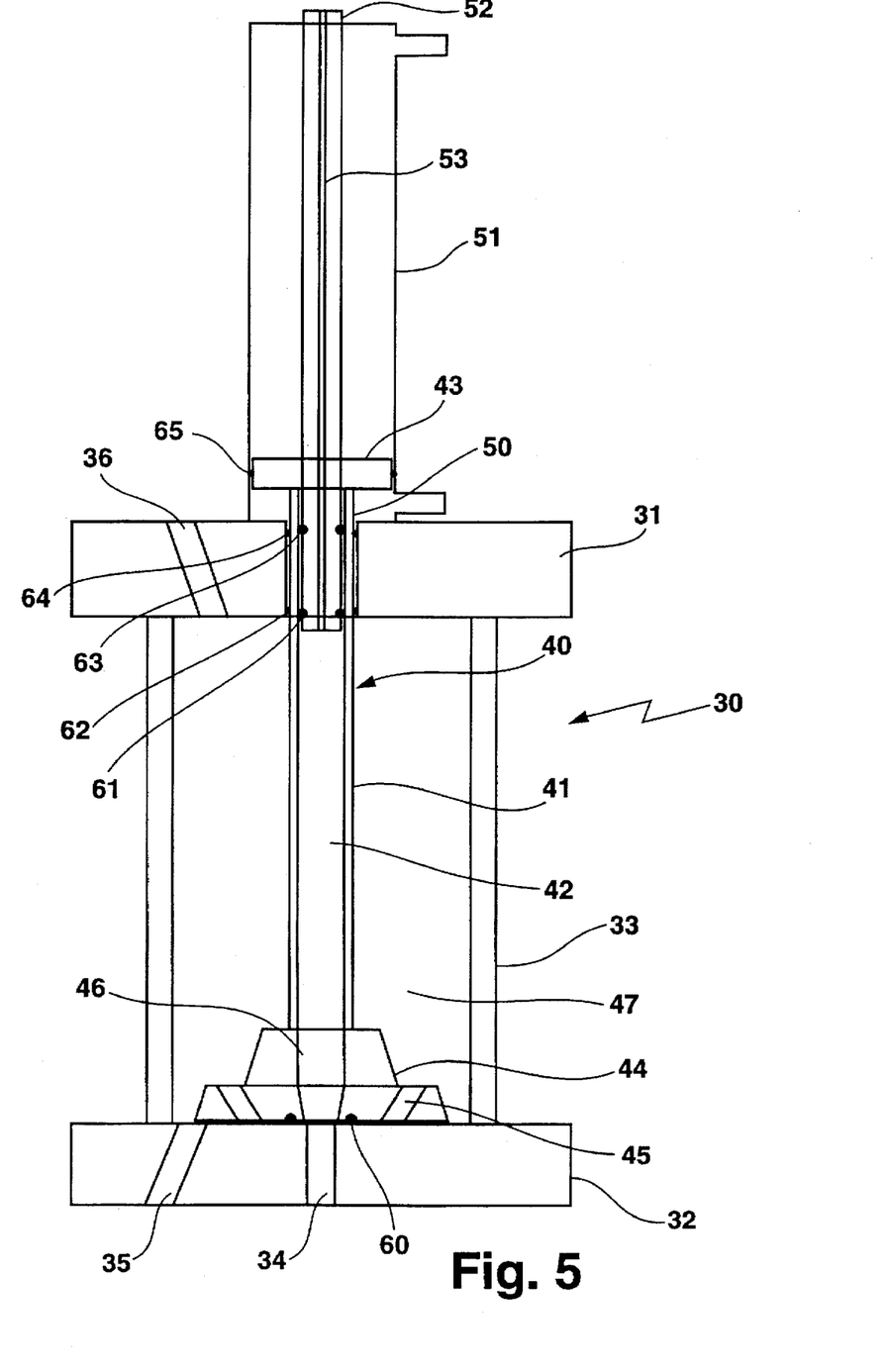
FIG. 5 shows another embodiment of the at least partially movable wall in accordance with the invention, wherein a cylindrically shaped mixing configuration is arranged coaxially within the measuring cell in a position sealingly separating and storing the two reaction liquids.
Figure 6:
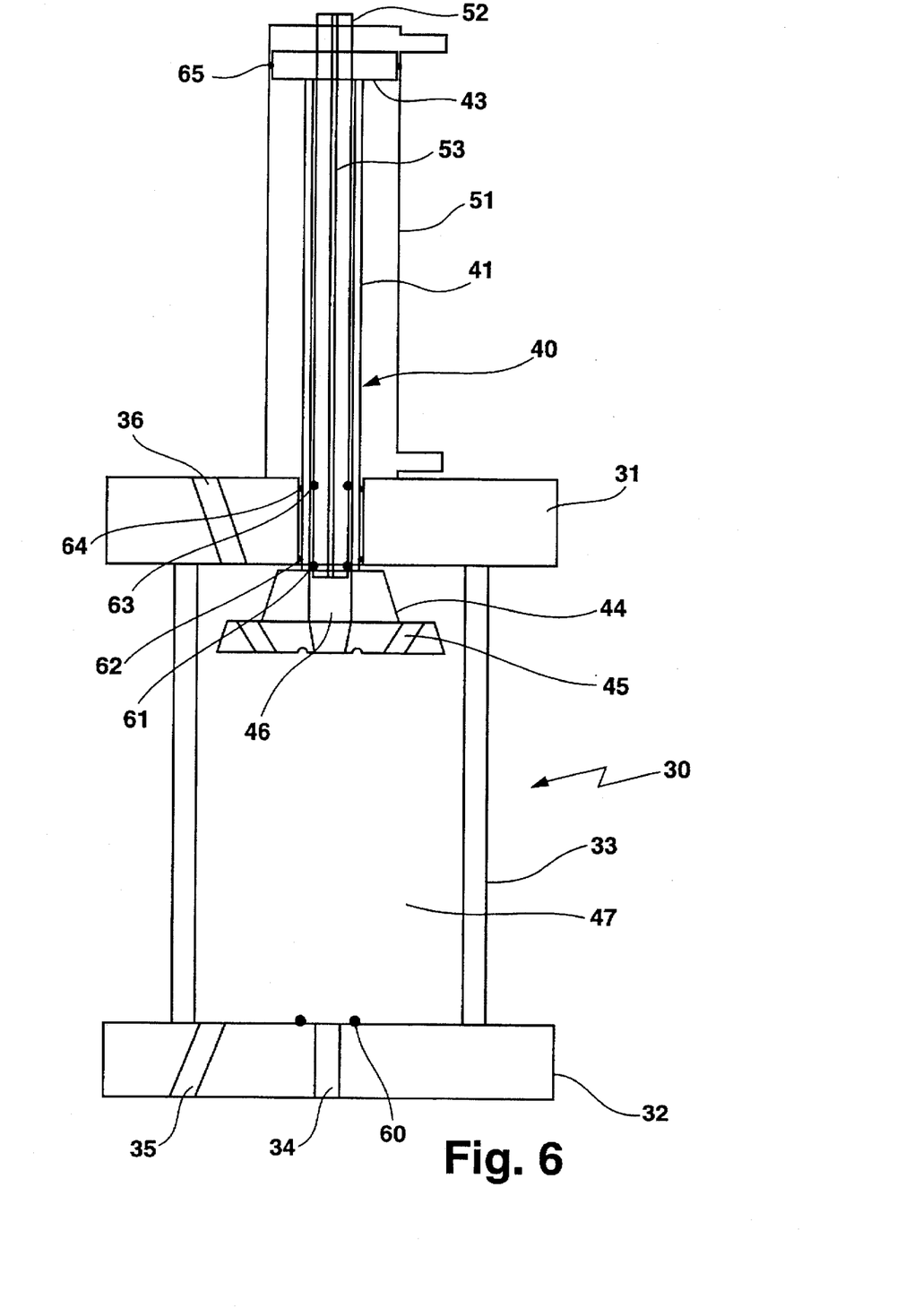
FIG. 6 is the configuration in accordance with FIG. 5 but in a retracted position.

A second embodiment in accordance with the invention is shown in FIGS. 5 and 6. The measuring cell 30 in accordance with the FIG. 5 has an upper component 31, a lower component 32 as well as a side wall 33 connecting the upper component 31 and the lower component 32. The side wall 33 is, for example, a hollow cylinder and a mixing plunger 40 is disposed centrally within the measuring cell 30. The mixing plunger 40 comprises a hollow cylinder 41 as well as a base 44. The base 44 has a central bore 46 which communicates with an inner region 42 of hollow cylinder 41. Bores 45 which travel diagonally through a lower portion of the base 44 cause an improved mixing of the reaction liquids as described below. The lower component 32 has a first inlet opening 34 which communicates with the central bore 46 of the base 44 or with the inner region 42 of the hollow cylinder 41. A second inlet opening 35 is disposed in the lower component 32 in such a fashion that it communicates with an outer region 47 of the measuring cell. In the embodiment in accordance with FIGS. 5 and 6, an outlet opening 36 for the outer reaction liquid is provided for in the upper component 31 of the measuring cell 30. A piston bore 53 serves as an outlet opening for the starting elements in the inner region 42 of the hollow cylinder 41.

A mount 51 is securely disposed on the upper component 31 of the measuring cell 30 and comprises a piston 52 having a central bore 53. The central bore 53 communicates with the inner region 42 of the hollow cylinder 41. The mixing plunger 40 has a disc-shaped device 43 at its upper end disposed in an interlocking fashion within the mount 51. The hollow cylinder 41 of the mixing plunger 40 is guided through an opening 50 in the upper component 31.

A seal 60 is provided for between the base 44 and the lower component 32 in order to separate the inner region 42 from the outer region 47 in a sealing fashion. Additional seals 61 and 63 separate the inner wall of the cylinder 41 from the outer wall of the piston 42 in a sealing fashion. Appropriate seals 62, 63 are provided for in order to seal the outer surface of the cylinder 41 with respect to the inner wall of the opening 50. A seal 65 is provided for around the outer periphery of the disc 43 to seal same with respect to the inner wall of the mount 51.

FIG. 6 shows the embodiment according to FIG. 5 but with the mixing plunger 40 withdrawn in the upper direction into the mount 51.

In order to operate the measuring cell configuration according to FIGS. 5 and 6, the mixing plunger 40 is initially lowered in a sealing fashion using seal 60, wherein the base 44 seats on the upper surface of the lower component 32. In this fashion the measuring cell 30 is subdivided into two separate chambers 42 and 47 which are sealed relative to each other. A first reaction liquid is introduced through the first inlet opening 34 or the central bore 46 into the inner region 42 of a hollow cylinder 41. In addition a second reaction liquid is introduced into the region 47 outside of the hollow cylinder but within the inner side wall of the measuring cell 30 by means of the second inlet opening 35. After the inner chamber 42 and the outer chamber 47 have been prepared and filled with reaction liquid, the mixing plunger 40 is pulled upwardly into the position shown in FIG. 6. The piston 52 drives the first liquid out of the inner region 42 of the cylinder 41 to flow out through the central bore 46 of the base 44. The base 44 can be provided with special bores 45 in order facilitate a more rapid and homogeneous mixture between the first and the second reaction liquids.

The movable plunger configuration 40 according to FIGS. 5 and 6 is also suitable for carrying out cyclically repeatable NMR measurements between at least two components in milliseconds following mixture. The base plate 32 of the measuring cell 30 has a off-center inlet bore 35 as well as a central bore 34 for filling the plunger 40. In the embodiment according FIGS. 5 and 6, the lid plate 31 has a single off-center drain bore 36 as well as a central bore 53 for the plunger overflow. The measuring cell 30 is preferentially manufactured from glass and comprises a glass tube of approximately 30 mm in height and 8 mm in diameter. It is advantageous when the plunger configuration 40 according to FIGS. 5 and 6 is made from plastic or glass having low proton content and comprises a special base configuration 44 for optimal mixing. A pneumatic unit for motion of the plunger 40 from the filling position in accordance with FIG. 5 into the measuring position in accordance with FIG. 6 can be advantageously disposed outside the measuring region. A sealing hollow guide pipe and o-ring seals can be arranged in FIGS. 5 and 6 according to need.

The selection of the inner diameter of the plunger 40 can be used to determine the ratio between the starting elements and the reagent. In the position in accordance with FIG. 5 the plunger 40 is closed by means of pressure on the disc 43 and both reagents are initially separated from each other. The inlets and outlets of the two chambers 47, 42 are connected to the probe head base by means of capillaries. The filling-up of the chambers 47 and 42 can be effected by means of injection or, ideally, using pumps. After NMR technical preparations of the starting elements and the reagents, mixing is effected through a rapid raising of the plunger 40 into the mount 51. This can be effected using pressurized gas in a lower pneumatic unit or through release of a biased spring. A special design of the base of the plunger 44, for example having diagonal bores 45, can facilitate an optimal mixing between both substances. Directly following the lifting of the plunger 40, the measurement is started. This procedure is configured in such a fashion that it can operate completely automatically and be repeated as often as desired.

The at least two reaction liquids can be stored in the measuring cell for pre-polarization and can be mixed following a certain pre-polarization time. A symmetric configuration of the at least partially movable wall facilitates the minimization of susceptibility perturbations. Although the embodiments describe the utilization of the mixing cell for two reaction liquids other embodiments and applications of the measuring cell in accordance with the invention for more than two components are possible.

We claim:

1. A NMR measuring cell suitable for use in a flow-through probe head to facilitate reactions between a first and a second reaction liquid comprising:

a NMR cell housing having a first inlet opening for introducing the first reaction fluid into the NMR cell and a second inlet opening for introducing the second reaction fluid into the NMR cell;

wall means disposed within said housing for subdividing said housing into a first chamber communicating with said first inlet opening and a second chamber communicating with said second inlet opening, said first chamber for storing the first reaction liquid and said second chamber for storing the second reaction liquid, wherein said wall means is adapted to move for mixing together the first and the second reaction liquids.

2. The NMR measuring cell of claim 1, wherein said first chamber has a first outlet opening and said second chamber has a second outlet opening.

3. The NMR measuring cell of claim 1, wherein said NMR cell housing is cylindrical in shape.

4. The NMR measuring cell of claim 1, wherein said wall means has mixing means.

5. The NMR measuring cell of claim 1, wherein said wall means comprises a first and a second component which are movable relative to each other and which interlockingly engage one another.

6. The NMR measuring cell of claim 5, wherein said first component comprises wings and said second component has windows and, in a first separating position of said wall means, said wings interlockingly engage said windows to separately store the first and second reaction liquids, and in a second mixing position of said wall means, said wings free said windows to mix the first and the second reaction liquids.

7. The NMR measuring cell of claim 5, wherein said first and second components are adapted for rotational motion relative to each other.

8. The NMR measuring cell of claim 5, wherein said first component rotates about an axis disposed vertically in a center of said housing and said second component is disposed in stationary fashion in said housing.

9. The NMR measuring cell of claim 6, wherein said first component rotates about an axis disposed vertically in a center of said housing and said second component is disposed in stationary fashion in said housing.

10. The NMR measuring cell of claim 5, wherein said wall means subdivides 2n chambers, with each chamber having an associated inlet opening, wherein n is a whole number.

11. The NMR measuring cell of claim 10, wherein said wall means has a cross-shaped cross section.

12. The NMR measuring cell of claim 1, wherein said wall means and said housing are adapted for partial removal of said wall means from said housing to effect mixing between the first and the second reaction liquids.

13. The NMR measuring cell of claim 12, further comprising a seal disposed between said wall means and said housing to store the first and the second reaction liquids in a sealing fashion in said first and said second chambers.

14. The NMR measuring cell of claim 12, wherein said wall means has mixing means.

15. The NMR measuring cell of claim 12, wherein said wall means is adapted for motion parallel to a longitudinal axis of said housing for mixing the first and second reaction liquids.

16. The NMR measuring cell of claim 12, wherein said wall means is adapted for motion through an upper end of said housing.

17. The NMR measuring cell of claim 12, wherein said wall means comprises a pipe-shaped component and said first chamber is located within said pipe-shaped component and said second chamber is formed between a housing wall and an outer surface of said pipe-shaped component.

18. The NMR measuring cell of claim 17, wherein said pipe-shaped component is hollow and cylindrical and said housing has a ring-shaped gap in an upper end thereof and a mixing together of the first and second reaction liquids is effected through withdrawal of said pipe-shaped component through said ring-shaped gap.

19. The NMR measuring cell of claim 12, wherein said wall means comprises a base disposed on one end thereof and having larger radial extent than remaining portions of said wall means.

20. The NMR measuring cell of claim 19, wherein said base has at least one of diagonal bores and wings.

21. A method for rapid mixing of a first and a second reaction liquid in a NMR measuring cell suitable for use in a flow-through probe head comprising the steps of:

disposing wall means within the cell for subdividing the cell into a first chamber communicating with a first inlet opening and a second chamber communicating with a second inlet opening, said first chamber for storing the first reaction liquid and said second chamber for storing the second reaction liquid;

introducing the first reaction fluid into said first chamber via said first inlet opening;

introducing the second reaction fluid into said second chamber via said second inlet opening;

moving said wall means to mix together the first and the second reaction liquids.

22. The method of claim 21, further comprising the steps of:

separating an elution corresponding to a chromotograph signal peak (LC peak) from a column of a liquid chromotograph apparatus (LC column); and introducing said elution as a reaction liquid on-line into a chamber of the measuring cell.

* * * * *